United States Patent [19]
Flower

[11] Patent Number: 5,895,369
[45] Date of Patent: Apr. 20, 1999

[54] IONTOPHORESIS PATCH/CONTROLLER INTERCONNECTION USING A CONDUCTIVE ELASTOMER TO PROVIDE NOISE-FREE ELECTRICAL CONTACT BETWEEN PATCH AND CONTROLLER

[75] Inventor: Ronald J. Flower, Vernon, N.J.

[73] Assignee: Becton Dickinson and Company, Franklin Lakes, N.J.

[21] Appl. No.: 08/825,976

[22] Filed: Apr. 4, 1997

Related U.S. Application Data

[63] Continuation of application No. 08/315,532, Sep. 30, 1994, abandoned.
[51] Int. Cl.$^6$ ................................................. A61N 1/30
[52] U.S. Cl. ................. 604/20; 607/152; 439/67
[58] Field of Search ................ 604/20–21; 607/149, 607/152; 439/67, 260, 267, 495, 725, 909

[56] References Cited

U.S. PATENT DOCUMENTS

| | | | |
|---|---|---|---|
| 3,319,216 | 5/1967 | McCullough | 439/67 |
| 4,451,694 | 5/1984 | Harper et al. . | |
| 4,505,848 | 3/1985 | Kobayashi . | |
| 4,636,786 | 1/1987 | Haertling . | |
| 4,642,627 | 2/1987 | Hodsdon . | |
| 4,695,258 | 9/1987 | Hanson et al. | 439/67 |
| 4,844,784 | 7/1989 | Suzuki et al. . | |
| 5,087,242 | 2/1992 | Petelenz . | |
| 5,415,629 | 5/1995 | Henley | 604/20 |
| 5,498,235 | 3/1996 | Flower | 604/20 |

FOREIGN PATENT DOCUMENTS

| | | | |
|---|---|---|---|
| 652135 | 6/1991 | Australia | 604/20 |

*Primary Examiner*—Mark Bockelman
*Attorney, Agent, or Firm*—Hoffman & Baron, LLP

[57] ABSTRACT

An iontophoretic drug delivery system having a patch including a medicament containing surface, and a controller having circuits which supply electric current to effect the iontophoretic drug delivery. The patch is detachably coupled to the controller and includes a plurality of spaced-apart electrical contacts. The controller includes an elastomeric connector which is made of alternating sections of electrically conductive and electrically non-conductive material. The electrically conductive material of the elastomeric connector is coupled to the controller circuiting. During transcutaneous drug delivery, the patch is connected to the controller such that the electrically conductive sections of the elastomeric connector are also coupled to respective spaced-apart electrical contacts of the patch so that the controller can control the rate and duration of the drug delivery.

13 Claims, 4 Drawing Sheets

5,895,369

1

IONTOPHORESIS PATCH/CONTROLLER INTERCONNECTION USING A CONDUCTIVE ELASTOMER TO PROVIDE NOISE-FREE ELECTRICAL CONTACT BETWEEN PATCH AND CONTROLLER

This application is a continuation of application Ser. No. 08/315,532, filed on Sep. 30, 1994 now abandoned.

BACKGROUND OF THE INVENTION

1. Field of the Invention

The present invention relates to iontophoretic drug delivery systems for transdermally delivering a drug or medicine to a patient, and more specifically relates to a connector which electrically couples a drug-containing patch and a controller.

2. Description of the Prior Art

Iontophoresis may be defined as the non-evasive transdermal delivery of medicine/chemicals. This process has become an increasingly popular and effective method for the delivery of pharmaceuticals. In practice, the process of iontophoretic drug delivery is typically achieved by placing a medicine (in ionic form) on a carrier, and attaching the medicine-containing carrier upon a patient's skin. A pair of electrodes are placed in contact with the patient's skin and in close proximity with the carrier. An electric current is provided by the electrodes through the skin. The electric current causes the ionic medicine to diffuse from the carrier of the patch through the skin.

Delivery of a drug to a patient iontophoretically may be best accomplished in a number of ways, such as at a constant rate over a long time period, or periodically at regular intervals. In order to ensure proper drug delivery, it is necessary for the drug-containing carrier to be maintained in contact with the patient's skin. The iontophoretic delivery system may include a drug-containing carrier such as an adhesive patch. The system may also include a source of electric power which is connectable to the patch for providing the proper electric current for transmission of the drug in accordance with the desired rate of delivery.

The electrical connections between the patch and controller in known drug delivery devices typically utilize resiliently biased conventional mechanical contacts. With this type of connection, wear and corrosion on the resiliently biased contacts from the repeated cycling of connection and removal of the patch with respect to the controller and from environmental conditions may have a deleterious effect on the contacts. The deleterious effects include the abrupt cessation of current delivery to the patch due to the "making and breaking" between the contacts. These current transients which may be produced may result in an uncomfortable sensation to the patient.

In transdermal delivery devices where the controller is detachable from the patch, the materials utilized on the patch and controller for electrical coupling must be electrochemically compatible with one another. Otherwise, electrolysis and corrosion may result affecting the quality of the electrical connection. This may result in electrical noise or current transients which may cause patient discomfort.

OBJECTS AND SUMMARY OF THE INVENTION

It is an object of the present invention to provide an iontophoretic drug delivery device including an electrical connector which permits the reliable electrical interconnection between a drug delivery patch and a detachable controller.

2

It is a further object of the present invention to provide an iontophoretic drug delivery controller having an electrical connector which is not subject to electrolysis and/or corrosion.

It is yet another object of the present invention to provide an iontophoretic drug delivery device having an electrical connector which overcomes the disadvantages of known electrical connectors of iontophoretic drug delivery devices.

In accordance with one form of the present invention, the apparatus includes a medicament containing disposable patch removably attached to a patient's skin in combination with a controller which electrically controls the delivery of the medicament. The patch includes a flexible planar body having a first surface containing the medicament, an opposed second surface and an extending planar tab for insertion within a region of the controller. The first surface of the planar patch body is supportable on the skin of the patient. The opposed second surface of the patch body has the controller removably attached thereto. The patch is secured to the controller by inserting the tab within the controller. The tab of the patch body includes a plurality of spaced-apart electrical contacts that are coupled to at least first and second spaced-apart electrodes which, when a voltage is applied thereto, induces an electric current flow which transmits the medicament from the patch to the patient's skin.

The controller may include a power supply for providing a source of electric current and a circuit mounted on a printed circuit board for controlling the power supply. The controller also includes an elastomeric connector which is positioned to engage the printed circuit board of the controller and the tab on the patch. The elastomeric connector includes a plurality of spaced-apart parallel conductive sections, while the printed circuit board includes a plurality of spaced-apart electrical contacts. Each of the contacts engages at least one of the plurality of conductive sections. The elastomeric connector is positioned such that when the tab of the patch body is inserted within the controller, the spaced-apart electrical contacts are respectively electrically coupled to at least one of the plurality of spaced-apart conductive sections of the elastomeric connector so that the at least first and second electrodes are electrically coupled to the power supply and printed circuit board of the controller.

DETAILED DESCRIPTION OF THE PREFERRED EMBODIMENTS

Figure 1:
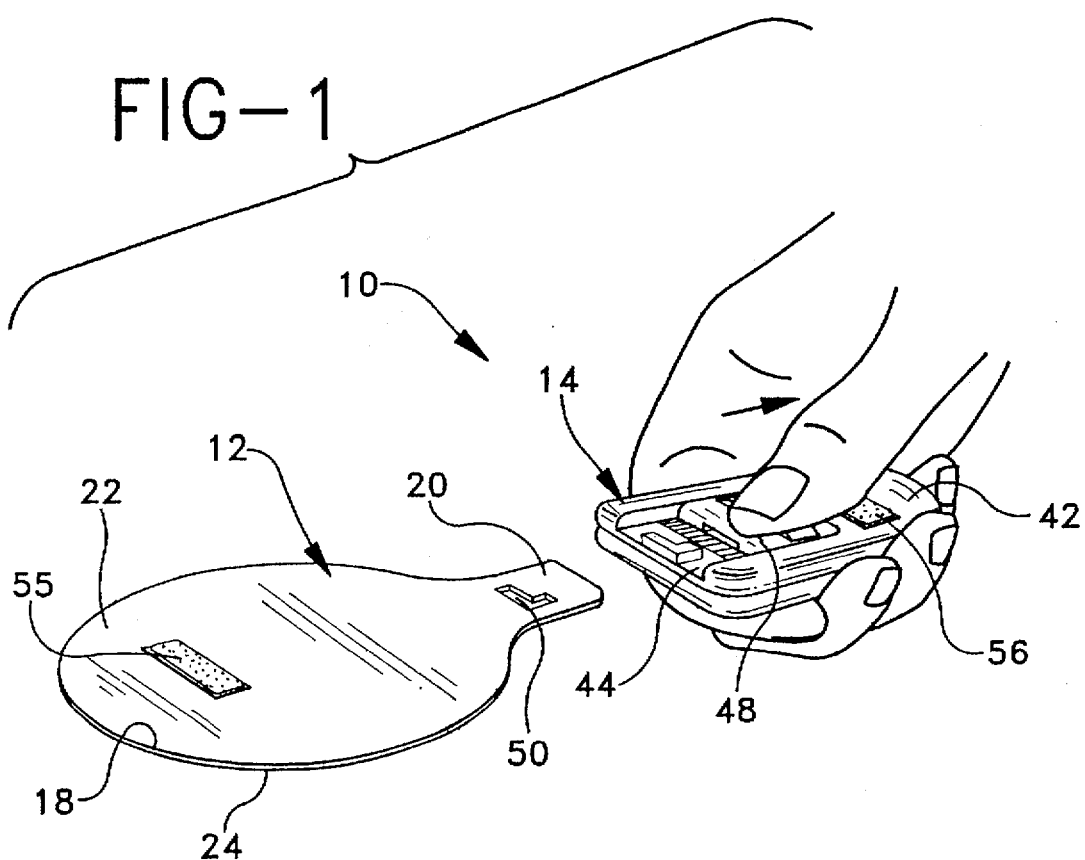
FIG. 1 is a top perspective view of the iontophoretic drug delivery system of the present invention wherein a patch and controller are in a disconnected configuration.
Figure 2:
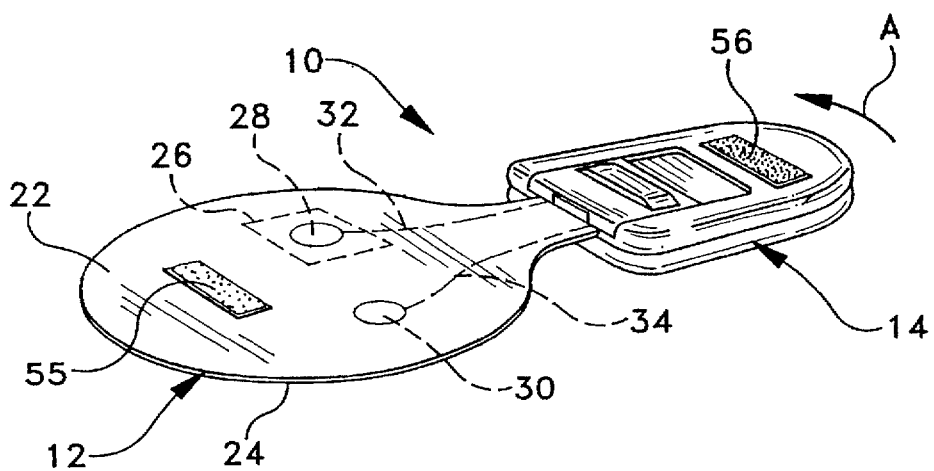
FIG. 2 is a top perspective view of the iontophoretic drug delivery system of the present invention wherein a patch and controller are in a connected configuration.
Figure 6:
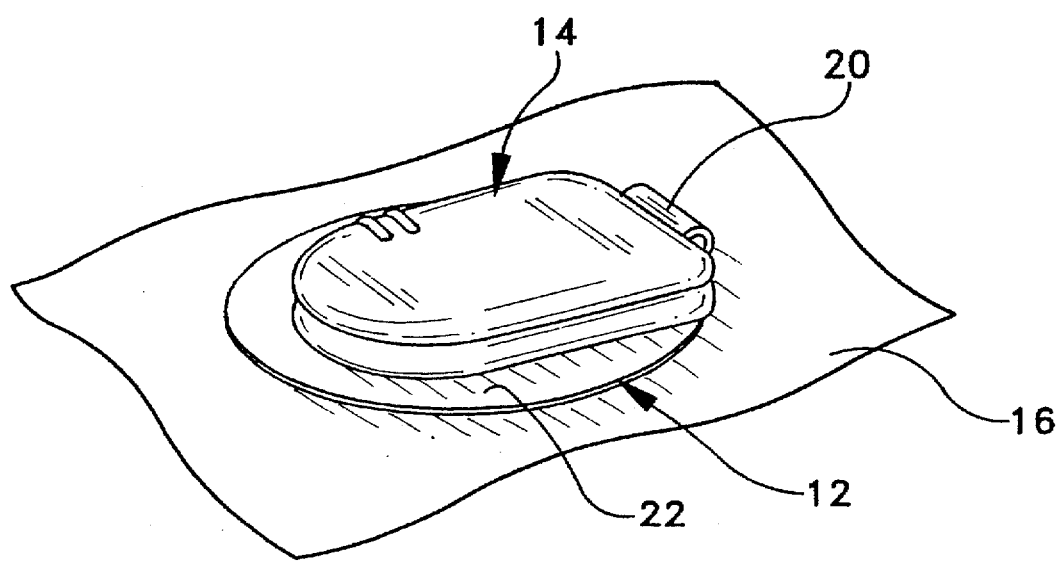
FIG. 6 is a top perspective view of the iontophoretic drug delivery system of the present invention wherein the patch is supported on the skin of a patient and the controller is connected to the patch.

Referring initially to FIGS. 1 and 2 of the drawings, an iontophoretic drug delivery system 10 basically includes a patch 12 and a controller 14. Patch 12 is a generally planar flexible member formed of biocompatible material. Patch 12 may be formed of woven or non-woven textiles or polymers or any other material as is well known in the art. Patch 12 preferably includes an adhesive (not shown) which permits the patch to be attached to the skin 16 of the patient (FIG. 6). In the preferred embodiment, patch 12 includes an enlarged substantially circular body 18 and an extending narrow tab 20. Patch body 18 includes opposed planar surfaces 22 and 24. Planar surface 24 is disposed for attachment to a patient's skin and includes a drug reservoir 26 which contains an ionic pharmaceutical which is typically in gel form. While reservoir 26 is shown in the Figures, any other technique may be employed which effectively stores an ionic medicament for transmittal to the patient's skin.

Skin contacting surface 24 of the patch may further include at least a pair of spaced apart electrodes 28 and 30. Each of electrodes 28 and 30 are positioned to be in contact with the skin when the patch 12 is attached thereto. The electrodes 28 and 30 are positioned such that an electric current path is established between the electrodes 28 and 30 through the skin of the patient. Electrode 28 is also electrically coupled to reservoir 26 in a manner well-known in the iontophoretic drug delivery industry. A direct current source may be coupled to the electrodes 28 and 30 such that electrode 28, which is in contact with reservoir 26, assumes the same charge as the ionized drug contained therein. Under the influence of electrical current passing from electrode 28 to electrode 30 through the skin, the drug contained in reservoir 26 is transcutaneously transmitted to the patient.

Figure 3:
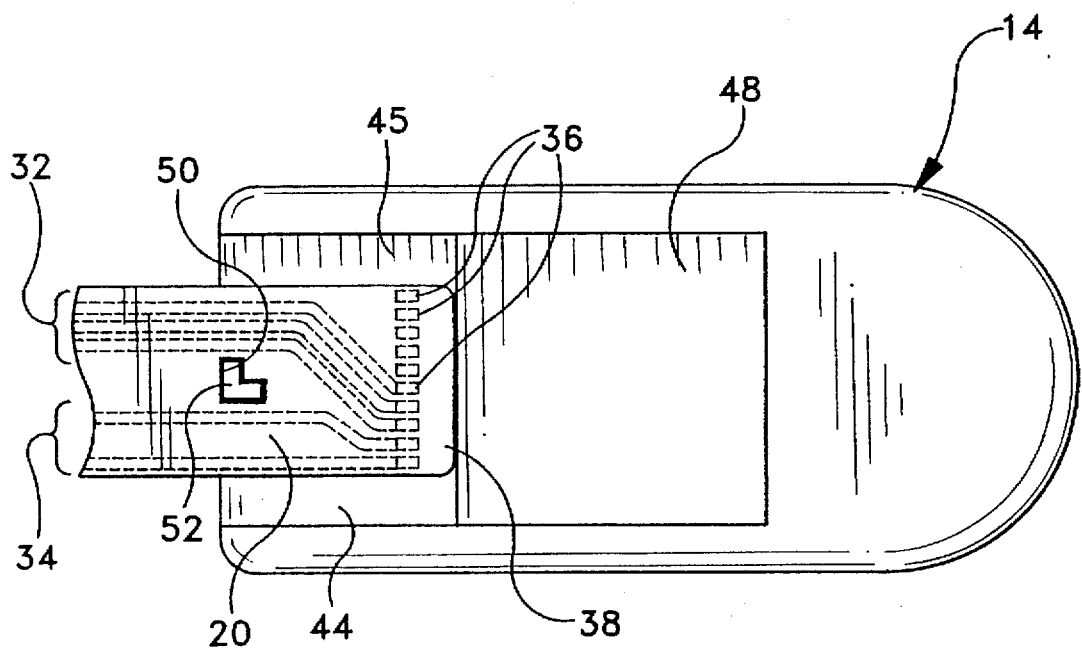
FIG. 3 is a top plan view of a portion of the patch and controller combination of FIG. 2.

Referring now to FIG. 3, electric current is supplied to electrodes 28 and 30 via electrical traces 32 and 34. Each of traces 32 and 34 may include one or more conductive paths extending from electrodes 28 and 30 to electrical contacts 36 positioned on a marginal edge 38 of tab 20. As will be described in further detail hereinbelow, electrical contacts 36 are optimally positioned for electrical connection to the controller 14 and its source of electric current.

Figure 4:
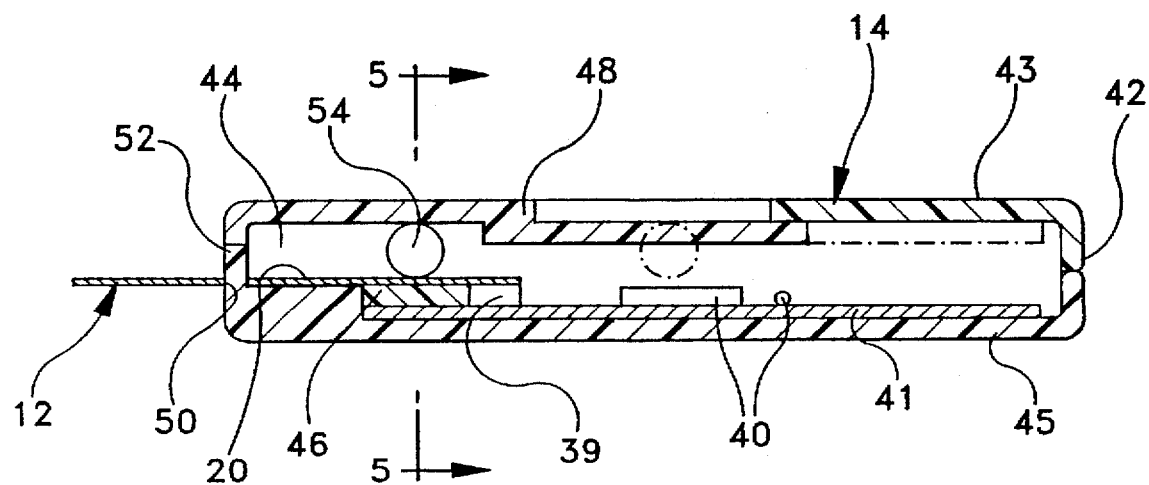
FIG. 4 is a cross-sectional view of the patch and controller combination of FIG. 3 taken across line 4—4.
Figure 5:
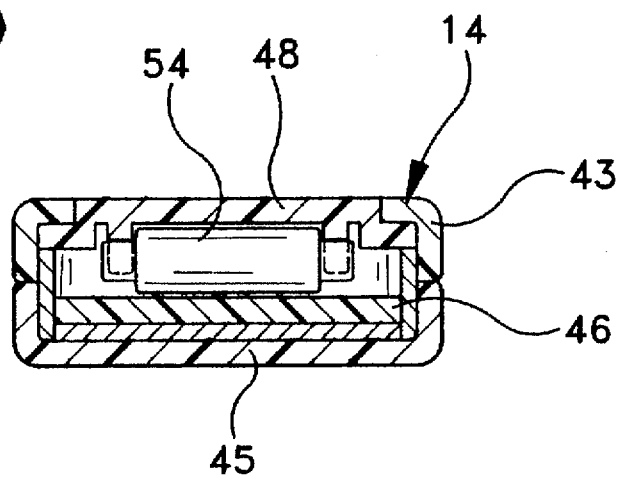
FIG. 5 is a cross-sectional view of the patch and controller combination of FIG. 4 taken along line 5—5.

Referring now to FIG. 4, controller 14 houses electronic components 40 which provide the controlled application of electric current to electrodes 28 and 30. As is known in the art, and in the preferred embodiment, the electrical components 40 include a source of electrical power such as a power supply 39. The electronic components and the power supply 39 may be mounted on a printed circuit board 41. The circuit of the controller is used to send a controlled electric current to electrodes 28 and 30.

Controller 14 includes a controller housing 42, having an upper wall 43. The controller also includes a cover 48 and a bottom wall 45. As shown in FIG. 1, cover 48 may be manually moved to an open position exposing connection array 46 for electrical connection with electrical contacts 36 of tab 20. With cover 48 in an open position, tab 20 of patch 12 may be electrically coupled to controller 14 via connection array 46. Cover 48 may similarly be moved to a closed position as shown in FIG. 2, substantially covering electrical contacts 36 of tab 20 along with connection array 46.

In order to ensure accurate alignment of electrical contacts 36 with corresponding segments of connection array 46, tab 20 includes a keyed opening to coincide to the structure of housing 42. Tab 20 includes an opening 50 which is designed to accept an upwardly extending post 52 of the housing. In a preferred embodiment, opening 50 and post 52 are generally rectangular in shape. However, any suitable configuration may be utilized. The controller also includes an open front end 44 which accommodates a suitable length of tab 20. Post 52 is centrally located adjacent connection array 46 so as to accommodate tab 20 and positionally confine tab 20 within housing 44. The key structure included on both opening 50 and post 52 prevents incorrect alignment of patch 12 with respect to controller 14. In the present embodiment, both opening 50 and post 52 have a generally L-shaped cross section, however, any other mating shape which would ensure correct alignment may be employed.

As mentioned above, housing 42 includes connection array 46 situated in electrical contact with printed circuit board 41. Connection array 46 may include a multiplicity of parallelly disposed, electrically conductive strips which are in electrical communication with the printed circuit board 41 and hence the components 40 mounted on the circuit board. The conductive strips of connection array 46 are also capable of being electrically coupled to the electrical contacts 36 of the patch when tab 20 is received by the opening 50 in the controller 14. In the present illustrative embodiment, printed circuit board 41 has a plurality of spaced-apart contacts 37 which the conductive strips of the array 46 engage.

As may be appreciated, suitable iontophoretic drug delivery of medicament contained in reservoir 26 to the skin of a patient is dependent upon both the amount and duration of current provided by electrodes 28 and 30. It is preferable that a good, clean electrical signal be provided across electrodes 28 and 30 so that proper transmission of the medicament is achieved. Further, as electric current is being passed directly through the skin of the patient, abrupt fluctuations in current flow between electrodes 28 and 30 may be felt by the patient. For example, the patient may encounter slight discomfort if the current applied across electrodes 28 and 30 spikes or otherwise fluctuates sharply. Such spikes or fluctuations can be caused by interference between the electrical connection of the connector array 46 and the patch contacts 36. The present invention ensures that good clean electrical connection is established and maintained between the conductive portions of the patch and the conductive portions of the controller, and also that there will not be any abrupt changes in the current due to variations in the impedance of the connection between the controller and the patch.

Figure 7:
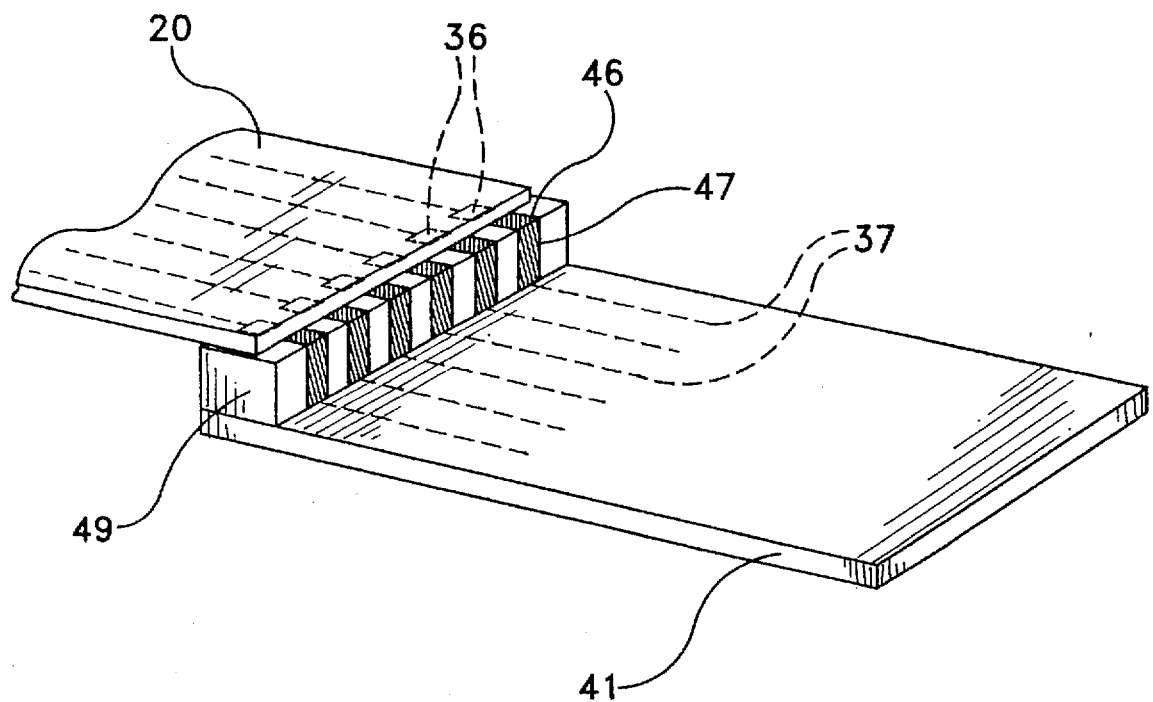
FIG. 7 is a perspective view of an elastomeric connector utilized in the present invention electrically coupling spaced-apart electrical contacts of a printed circuit board envisioned to be used in a controller of a drug delivery device with spaced-apart electrical contacts of a patch envisioned to be used in such a device.

In a preferred embodiment of the present invention and as shown in FIG. 7, the connection array 46 includes an elastomeric connector electrically coupled to the power supply 39 and circuit board 41. The elastomeric connector is made of elastomeric material and is preferably a "zebra" strip, which has alternating sections of electrically conductive material 47 and electrically non-conductive material 49 as known in the art. The zebra strip is a commercially available product and a suitable zebra strip is manufactured by Technit Corporation. Typically, the conductive portion is substantially carbon doped silicon while the non-conductive portion is substantially silicon. The conductive strips 47 may be spaced apart by only 0.005 inches, so that several conductive strips 47 may be in contact with the relatively wider contacts of the printed circuit board and patch to ensure a good connection between the patch and circuit board.

Referring to FIG. 7, the elastomeric connector is preferably securely affixed across the plurality of contacts 37 of the circuit board 41 for aiding in the electrical connection to the contacts. Preferably, the alternating strips of electrically conductive material 47 and electrically non-conductive material 49 are spaced-apart so as to contact correspondingly spaced contacts 37 of the printed circuit board 41. As shown in FIGS. 2, 4, and 7, when the tab 20 of patch 12 is inserted within the controller, the plurality of spaced-apart electrical contacts 36 of the patch coincide with and electrically couple to the electrically conductive portions 47 of the elastomeric connector 46. Therefore, as shown in FIG. 7, an electrical connection is achieved between the patch 12 and controller 14.

The zebra strip is preferred because it is capable of having plurality of electrical paths which permit conduction of electric current in two directions, but prevent electrical conduction in a third substantially orthogonal direction. By permitting electrical connection along two axis, the zebra strip can easily adapt to the devices to which it will be coupled and provide coupling with devices located in different planes. In addition, negligible electrical noise is created with the elastomeric connector. Furthermore, the elastomeric connector is an inert material so that there is no junction potential and no electrolysis or corrosion of the connector. As a result, the resistance of the connection between the patch and the controller will not fluctuate. Moreover, the elastomeric connector is a resilient material. Therefore, if pressure is applied to the connector, the connector will conform to the contour of the device to which it is coupled. This aids in providing a better electrical connection of the controller and patch. Finally, the elastomeric connector is non-abrasive and will not wear away the electrical contacts which are sometimes only painted on the surface of a device. This provides a better flow of current and no need to replace the connector or the devices to which it is attached because of wearing.

Figure 8:
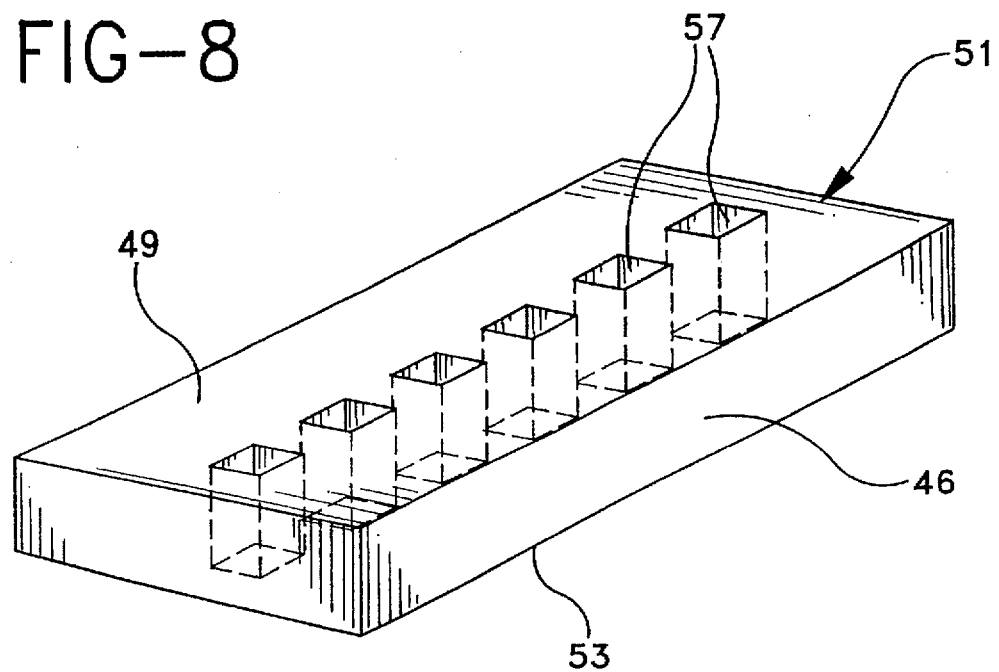
FIG. 8 is a top perspective view of the elastomeric connector utilized in an alternative embodiment of the present invention.

In an alternative form of the present invention and referring now to FIG. 8, the elastomeric connector 46 consists of a section of electrically non-conductive (insulative) material 49 having first and second surfaces 51, 53. The connector may also include a plurality of electrically conductive elastomeric plugs 57 which extend through the non-conductive material 49 from the first surface 51 to the second surface 53. This type of elastomeric connector is typically specifically designed to coincide with the lay-out of the spaced-apart electrical contacts of the patch to which the controller is coupled. The conductive elastomeric plugs are typically positioned on the connector so as to provide good electrical contact with the patch electrical contacts. In a preferred embodiment, the plugs are specifically dimensioned and positioned within the elastomeric connector so that the conductive plugs will contact only one of the spaced apart electrical contacts of the patch. This type of connector is affixed to the printed circuit board 41 as previously described.

In order to ensure that adequate electrical coupling between electrical contacts 36 of tab 20 and the connection array 46 is maintained, cover 48 carries a captively retained pressure roller 54. As shown in FIG. 4, the roller 54 is movable upon closure of cover 48 over electrical contacts 36 of tab 20 and connection array 46 to force electrical contacts 36 onto the conductive portions of connection array 46 establishing good electrical connection therebetween. The engagement of roller 54 also serves to secure patch 12 in connection with controller 14.

Referring again to FIG. 2, patch 12 and controller 14 include attachment means so as to permit the releasable support of controller 14 on patch 12 after interconnection between electrical contacts 36 and connective array 46 is established. Surface 22, which is opposed to skin-engaging surface 24 of patch 12, and the upper surface of housing wall 43 include cooperating fastening elements 55 and 56. In the present illustrative embodiment, the cooperative fastening elements include conventional hook and loop fasteners of the type sold under the trademark VELCRO. One cooperating fastening element 55 is secured adhesively or otherwise to patch 12 on surface 22 while the other cooperating fastening member 56 is secured by adhesive or otherwise to the upper surface of wall 43 of housing 42. As will be described in further detail hereinbelow, attachment of the mating hook and loop fasteners 55 and 56 provides for removable support of controller 14 on patch 12.

Having described the components of the patch and controller assembly 10 of the present invention, its operation will now be described.

Patch 12 may be adhesively secured to the skin 16 of the patient. Surface 24 of patch 12 is placed in intimate contact with the skin 16 so that electrodes 28 and 30 as well as drug-containing reservoir 26 are supported in good intimate contact with the skin 16. In order to initiate transcutaneous iontophoretic drug delivery from reservoir 26, controller 14 is connected to patch 12. Cover 48 is retracted rearwardly opening front end 44 of controller 14. Housing 42 is slipped over extending tab 20 of patch 12 so that opening 50 in tab 20 is seated over upwardly extending post 52 of housing 42. Proper planar orientation is assured between patch 12 and controller 14 due to the key matability between opening 50 and post 52. Cover 48 is then slid forwardly, closing cover 48 over tab 20.

The captively retained roller 54 is provided over tab 20 forcing electrical contacts 36 into secure electrical engagement with the conductive portions of connection array 46. The conductive portions of connection array 46 are also electrically coupled to the spaced-apart conductive runners 37 of the printed circuit board 41 within the controller. Closure of cover 48 prevents removal of patch 12 from controller 14 as cover 48 overlies post 52. As controller 14 is designed to be left in electrical connection with patch 12 during drug delivery, controller 14 may be fastened to patch 12 so that it will be conveniently retained on the skin of the patient. As shown in FIG. 2, once patch 12 is connected to controller 14, the controller may be flipped up in the direction of arrow A so that the mating hook and loop fasteners 55 and 56 engage each other to removably fasten controller 14 to patch 12 as show in FIG. 6. The controller 14 is comfortably retained on the skin of the patient during iontophoretic drug delivery. When the particular drug delivery is complete, the controller may be removed by separating the mating hook and loop fasteners 55 and 56. Cover 40 may then be retracted, exposing post 52 permitting removal of tab 20 from controller 14. The controller may be then placed aside until the next administration of the drug is needed. The patch 12 may remain on the skin of the patient, eliminating the need for frequent replacement of the patch.

Although it has been described that the elastomeric connector is mounted in the controller housing, it is envisioned to be within the scope of this invention to mount the elastomeric connector on the patch to mate with the printed circuit board of the controller.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed:

1. An iontophoretic drug delivery system for delivering medication to an applied area of a patient comprising:
   an iontophoretic drug delivery patch for placement against the skin of a patient, the iontophoretic drug delivery patch including a flexible support base having thereon a medicament, at least first and second electrodes, and an integrally formed tab supporting a plurality of spaced-apart electrical contacts, at least a first electrical contact and a second electrical contact of the plurality of spaced-apart electrical contacts being respectively electrically coupled to the at least first and second electrodes; and
   a controller having an outer housing and including a portion mateable with the flexible tab of the iontophoretic drug delivery patch, the controller housing including therein electronic components for controlling current provided to the electrodes of the iontophoretic drug delivery patch, at least two controller contacts, and an elastomeric connector, the elastomeric connector being disposed between and electrically in contact with the at least two contacts of the controller and the at least first and second electrical contacts of the iontophoretic drug delivery patch when the controller is mated with the iontophoretic drug delivery patch.

2. An iontophoretic drug delivery system as defined by claim 1, wherein the elastomeric connector comprises alternating sections of electrically conductive and electrically insulative material.

3. An iontophoretic drug delivery system as defined by claim 1, wherein the elastomeric connector enables a substantially constant current flow from the controller to the iontophoretic drug delivery patch.

4. An iontophoretic drug delivery system as defined by claim 1, wherein the elastomeric connector includes at least first and second electrically conductive sections and a first electrically insulative section, the first electrically insulative section preventing a current flow between the first conductive section and the second conductive section.

5. An iontophoretic drug delivery system as defined by claim 1, wherein the elastomeric connector includes a plurality of spaced-apart transverse conductive sections, at least one of the plurality of spaced-apart electrical contacts engaging at least one of the plurality of conductive sections so as to electrically couple a corresponding spaced-apart electrical contact of the iontophoretic drug delivery patch to the controller.

6. An iontophoretic drug delivery system as defined by claim 1, wherein the controller housing includes a printed circuit board having a plurality of spaced-apart electrical contacts, the elastomeric connector being electrically coupled to at least one of the plurality of spaced-apart electrical contacts of the printed circuit board, the elastomeric connector electrically coupling the at least one of the plurality of spaced-apart electrical contacts of the iontophoretic drug delivery patch to the at least one of the plurality of spaced-apart electrical contacts of the printed circuit board.

7. An iontophoretic drug delivery system as defined by claim 1, wherein the elastomeric connector includes a first electrically conductive section and a first electrically insulative section.

8. An iontophoretic drug delivery system as defined by claim 1, wherein the elastomeric connector comprises alternating sections of electrically insulative inert material and electrically conductive inert material to substantially eliminate corrosion and/or electrolysis at the connector assembly.

9. An iontophoretic drug delivery system for delivering medication to an applied area of a patient comprising:
   an iontophoretic drug delivery patch for placement against the skin of the patient, the iontophoretic drug delivery patch including a medicament, at least first and second electrodes and a flexible tab supporting a plurality of spaced-apart electrical contacts, at least a first electrical contact and a second electrical contact of the plurality of spaced-apart electrical contacts being respectively electrically coupled to the at least first and second electrodes; and
   a controller having an outer housing and including a portion mateable with the flexible tab of the iontophoretic drug delivery patch, the controller housing including therein electronic components for controlling currents provided to the electrodes of the iontophoretic drug delivery patch, at least two controller contacts, and an elastomeric connector, the elastomeric connector including a substantially compliant electrically insulative material having first and second surfaces, the elastomeric connector also including a plurality of conductive plugs, each of the plurality of conductive plugs extending through the electrically insulative material from the first surface to the second surface such that the conductive plugs are only exposed on the first and second surfaces of the insulative material and are otherwise completely surrounded by the insulative material, the elastomeric connector being disposed between and electrically in contact with the at least two contacts of the controller and the at least first and second electrical contacts of the iontophoretic drug delivery patch, and wherein the controller housing includes an external actuator for selectively mating said patch contacts and said elastomeric connector when the controller is mated with the iontophoretic drug delivery patch.

10. An iontophoretic drug delivery system as defined by claim 9, the plurality of conductive sections being disposed within the electrically insulative material so as to electrically couple at least one of the plurality of conductive sections with at least one of the plurality of spaced-apart electrical contacts of the iontophoretic drug delivery patch when the controller is mated thereto.

11. An iontophoretic drug delivery system as defined by claim 9, wherein the electrically insulative material and the conductive plugs are made of inert materials to substantially eliminate corrosion and/or electrolysis at the connector assembly.

12. An iontophoretic drug delivery controller, the iontophoretic drug delivery controller being mateable with an iontophoretic drug delivery patch having at least first and second electrodes and a plurality of spaced-apart electrical contacts, the iontophoretic drug delivery controller substantially manipulating the delivery of a medicament retained by the iontophoretic drug delivery patch, the iontophoretic drug delivery controller comprising an outer housing including a portion mateable with said patch and having therein:
   a printed circuit board having a plurality of spaced-apart electrical contacts electrically connected to electrical components for manipulating drug delivery; and
   an elastomeric connector including a plurality of spaced-apart transverse conductive sections, the elastomeric connector being electrically coupled to the spaced-apart electrical contacts of the printed circuit board, the plurality of spaced-apart electrical contacts of the printed circuit board being oriented so as to substantially contact correspondingly spaced conductive sections of the elastomeric connector, the elastomeric connector permitting the plurality of spaced-apart electrical contacts of the drug delivery patch to be substantially simultaneously coupled thereto;

and wherein the controller housing includes an external actuator for selectively mating said patch contacts and said elastomeric connector.

13. In combination:
  an iontophoretic drug delivery patch having a medicament-containing portion and a controller-interconnection portion, said controller-interconnection portion having a plurality of electrical contacts; and a controller having an outer housing including a portion mateable with said patch controller-interconnection portion and having therein electronic components for regulating current, the controller being detachably mated with the iontophoretic drug delivery patch, the controller housing including an elastomeric connector having a plurality of conductive portions electrically coupled to the electronic components of the controller housing, the plurality of conductive portions of the elastomeric connector being electrically coupled to the plurality of electrical contacts of the iontophoretic drug delivery patch, and wherein the controller housing includes an external actuator for selectively mating said patch contacts and said elastomeric connector.

* * * * *

UNITED STATES PATENT AND TRADEMARK OFFICE
CERTIFICATE OF CORRECTION

PATENT NO. : 5,895,369
DATED : April 20, 1999
INVENTOR(S) : Ronald J. Flower

It is certified that error appears in the above-indentified patent and that said Letters Patent is hereby corrected as shown below:

In Column 7, line 31, now reads, "delivery patch";

should read --delivery patch, and wherein the controller housing includes an external actuator for selectively mating said patch contacts and said elastomeric connector.--

Signed and Sealed this

Thirtieth Day of November, 1999

Attest:

Q. TODD DICKINSON

Attesting Officer

Acting Commissioner of Patents and Trademarks